United States Patent [19]

Shalon et al.

[11] Patent Number: 4,719,011

[45] Date of Patent: Jan. 12, 1988

[54] HIGH PRESSURE LIQUID CHROMATOGRAPHY COLUMNS

[75] Inventors: Yehuda Shalon, Clayton; Danny D. Meyer, St. Louis, both of Mo.

[73] Assignee: H. T. Chemicals, Inc., St Louis, Mo.

[21] Appl. No.: 5,641

[22] Filed: Jan. 21, 1987

Related U.S. Application Data

[63] Continuation of Ser. No. 714,730, Mar. 22, 1985, abandoned, which is a continuation-in-part of Ser. No. 492,802, May 9, 1983, Pat. No. Des. 285,290.

[51] Int. Cl.[4] .............................................. B01D 15/08
[52] U.S. Cl. ................................. 210/198.2; 210/261; 55/386
[58] Field of Search ...................... 210/656, 198.2, 261, 210/470, 471; 55/197, 386

[56] References Cited

U.S. PATENT DOCUMENTS

| | | | |
|---|---|---|---|
| 2,746,297 | 5/1956 | Martin | 210/470 |
| 3,483,986 | 12/1969 | Wright | 210/198.2 |
| 3,763,879 | 10/1973 | Jaworek | 210/198.2 |
| 4,389,313 | 6/1983 | Charney | 210/198.2 |
| 4,550,594 | 11/1985 | Engstrom | 210/198.2 |
| 4,554,071 | 11/1985 | Ruijten | 210/198.2 |

*Primary Examiner*—Ernest G. Therkorn
*Attorney, Agent, or Firm*—Paul M. Denk

[57] ABSTRACT

This invention relates to high pressure liquid chromatography and to chromatographic columns employed therein. These columns may be modularly modified as to length and/or internal diameter and may contain other components in the modular system, for example, column sections, adapters and cone adapters, for joining column sections of different internal diameters, and end plate units for funnelling in or discharging out fluids; said end caps or lids, with or without funnel shaped means, for facilitating the liquid entrance or exit; and porous frits, with or without handles, all used in conjunction with the column sections to facilitate their usage for performance of specific chromatographic functions. The column sections have terminal flange-like means for accommodating the joining together for formations of a system suitable for high pressure liquid chromatography of the preparative or semi-preparative type.

2 Claims, 32 Drawing Figures

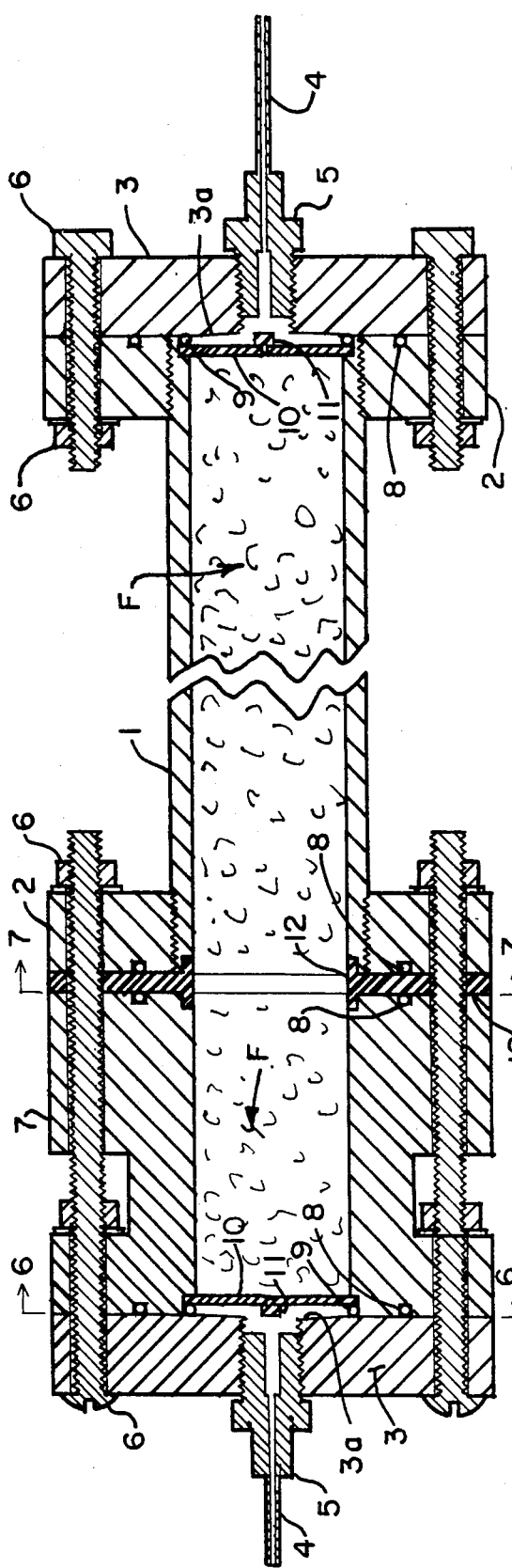
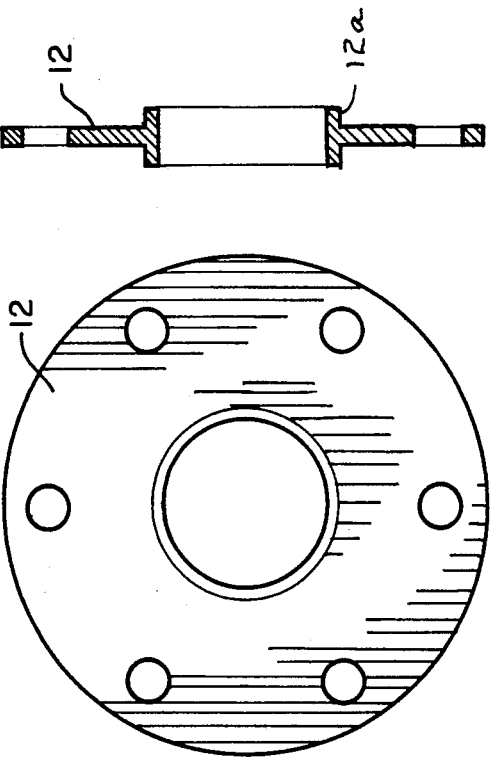
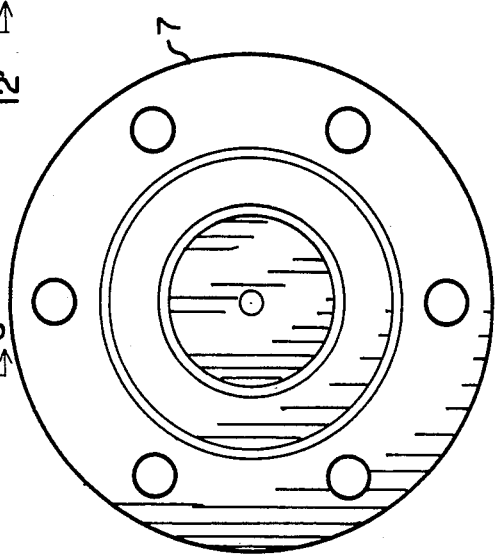
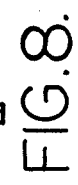
FIG.5.
FIG.6.
FIG.7.
FIG.8.

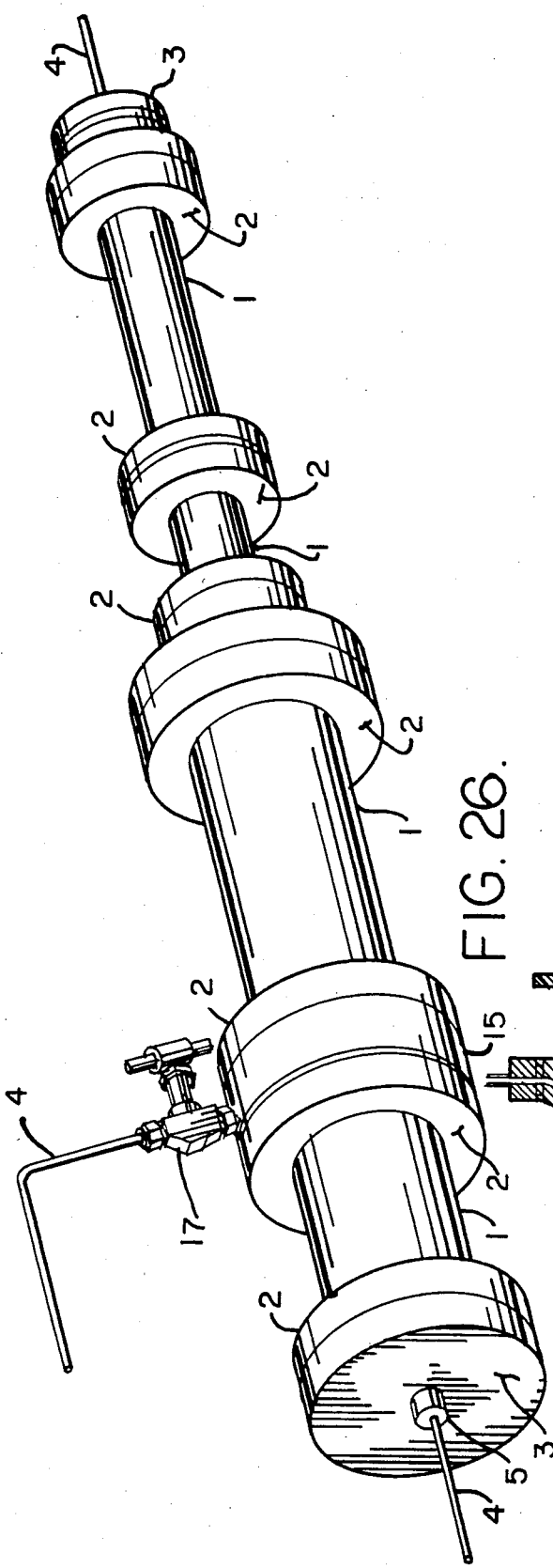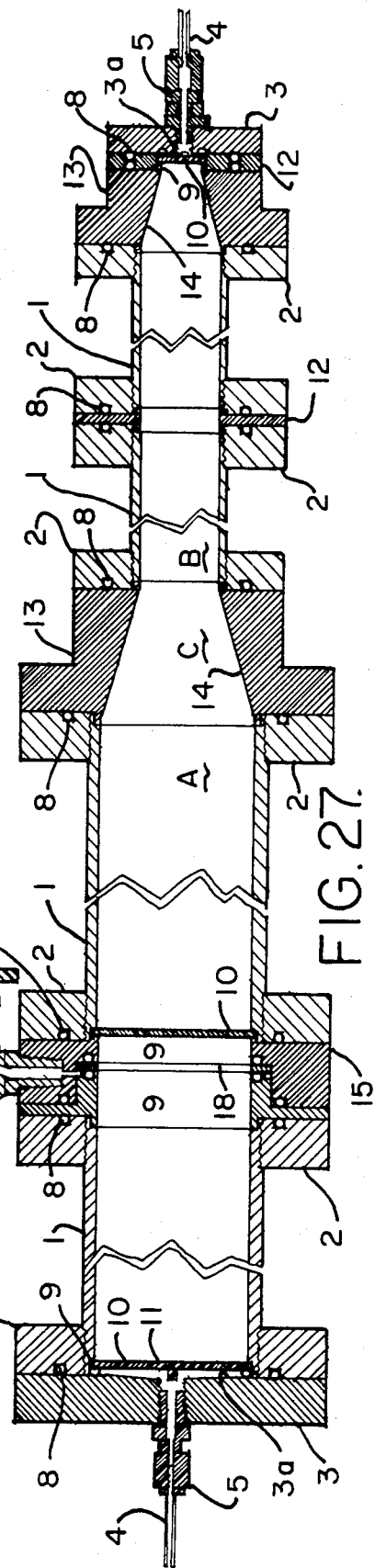
FIG. 26.
FIG. 27.

HIGH PRESSURE LIQUID CHROMATOGRAPHY COLUMNS

CROSS REFERENCE TO RELATED APPLICATION

This application is a continuation of the application having Ser. No. 714,730, filed on Mar. 22, 1985, now abandoned, and which application is designated as a continuation-in -part of the design application having Ser. No. 492,802, filed on May 9, 1983, now U.S. Pat. No. 285,290, all of said applications owned by a common assignee.

BACKGROUND OF THE INVENTION

This application relates to high pressure liquid chromatography (HPLC) and to chromatographic columns employed therein. More particularly, this invention relates to chromatographic columns which may be modularly modified as to length and/or internal diameter and to components employed therewith. This invention also relates to uses thereof.

Chromatography is a separation method whereby individual chemical compounds which were originally present in a mixture are resolved from each other by the selective process of distribution between two heterogenous (immiscible) phases. The distribution of chemical species to be separated occurs in a dynamic process between the mobile phase and the stationary phase. The stationary phase, or the column packing material, usually has a relatively large surface area, through which the mobile phase is allowed to flow. The chemical nature of the stationary phase exercises the primary control over the separation process. The greater the affinity of a particular chemical compound to the stationary phase, the longer it will be maintained in the system. The mobile phase can be either gas or liquid; correspondingly, the methods are referred to as gas chromatography and liquid chromatography.

There are four combinations of heterogenous phase systems, which give rise to four different chromatographic methods: gas-solid, liquid-solid, gas-liquid, and liquid-liquid chromatography. In gas-solid and liquid-solid chromatography, sample molecules are caused to interact physically with the surface of a porous solid by means of a phenomenon called adsorption. Hence, these two methods are also generally referred to as adsorption chromatography. The adsorption effect of the chromatographic column packing material determines their rates of migration through the column. In gas-liquid and liquid-liquid chromatography, the liquid stationary phase is held on the surface of an inert solid which serves merely as its support and, ideally, does not participate in the separation process. Primarily, then, the components of a mixture of chemicals having different solubilities in the stationary phase separate by migrating at different rates. The partitioning of the mixture between the two phases is the basis of these methods, they are also generally referred to as partition chromatography. The rate of migration of the various components of the mixture can be related to its thermodynamic partition coefficient in a given two-phase system.

Chromatography has been used primarily as a separation and isolation method. Unlike classical chemical separation methods (for example, precipitation or crystalization), chromatography is intended to separate many mixture components in a single-step procedure. Chromatographic methods can be applied to an incredible concentration range: although some separations can be performed in commercial-scale quantitites (e.g., milligrams to grams, grams to kilograms) which we refer to as preparative HPLC, and it is also feasible to carry out certain highly sensitive analytical determinations on the order of $10^{-9}$ g Chromatographic separations are based on the physiochemical principles of adsorption and partition, and, conversely, these and related fundamental phenomena can be studied by highprecision chromatography of model systems.

In liquid chromatography, the mobile phase may be percolated through the column at atmospheric pressure, by means of gravity, or under more contemporary precedures through pressure generated by a suitable pump. High pressure pumps which can generate up to several thousand atmospheres of inlet pressure are used.

Thus, high pressure liquid chromatography is a process of separating complex mixtures of chemicals by passing a solution of the chemicals through a stationary column packing material and under a certain degree of pressure. Preparative high pressure liquid chromatography is that process where one applies a mixture of a compound in a solution in its mobile phase where the selectivity of the components of the column packing material will retain the various and select components of the mixture for that length of time which causes its select components to be eluted discretely for separate collection as individual components and as purified elements. The efficiency of the columns is what makes such separation possible, and the efficiency of the columns depend upon such factors as the following:

(1) Length and/or width of the column.
(2) Type of medium.
(3) The mobile phase.
(4) Complex to be separated.

The eluted components are collected as fractions of the analyzed or prepared chemical mixture.

This invention, more specifically, relates to the configuration and structure of the columns used in high pressure liquid chromatography, and particularly in preparative chromatography. Through usage of the mechanisms of this particular invention the chromatographer can optimize preparative HPLC by permitting the best possible combinations of column internal diameters (ID) and lengths. This is readily accomplished by coupling columns of varying lengths through the use of the variety of adaptors employed in the build up of columns for use in the method of this invention. The system of this invention assembles quite easily mainly because all of its components are totally modular, and they are very convenient to handle.

With regard to the usage of this particular invention for preparative high pressure liquid chromatography, for performance of semi-preparative HPLC, which is used for separating miligram to gram quantities, the columns will normally be subjected to pressures up to approximately 2,000 psi. And, the type of columns suggested for usage are those which will have internal diameters of between about ½ inch to 1 inch. Usage of this current invention for preparative HPLC, such as for heavier loadings of grams to 10 grams quantities, the type of columns recommended would be those within a range of having an internal diameter of between about 1 inch to 4 inches in dimension, and which also functions up to approximately 2,000 psi of pressure. In process liquid chromatography, which includes the separations of grams to kilogram quantities, it is recommended that the modular columns of this invention incorporate internal diameters of between about 4 inches, or through columns having diameters approximating 5 inch or 6 inch, or even above. And, the pressure rating for these type of columns generally is within the range of 150 psi of pressure. Column sections obtainable for usage in conjunction with the teachings of this invention are available in a variety of lengths, as from 5 centimeters, or less, up to 100 centimeters, or more, and may include diameters up to approximately 20 inches. Thus, it can be readily seen that the flexibility that is built into the modularization or combination of chromatographic columns in conjunction with this invention add significant flexibility to the processes that can be undertaken by the lab technician, and by using the variety of additional adaptor components to be subsequently analyzed, such as a cone adaptor, or regular adaptor, including end plates, a variety of chromatographic columns having differing internal diameters can be achieved, and function quite effectively to attain the desired results. Another unique feature of this type of invention is that it may be used when heavier loadings of the chromatographic columns are desired.

Lengthwise, the various preparative columns, whether it be of the semi-preparative type, for use in preparative HPLC, or for process HPLC, normally such columns are available in lengths of approximately 5 cm up to 100 cm in length. Although, HPLC, normally column lengths, of the 4 inch type, usually begin with a minimum length of approximately 20 cm. The semipreparative column is considered to be a column with an internal diameter, as previously explained, of about a ½ in. or 1 in., and more generally is in the 30 or 50 cm of length category, packed with particles of between about 10 microns to 40–60 microns. Although, this current invention has been found to function quite effectively even with shorter length columns, particularly since the various columns of this particular invention are of the modular type, and can be built up one upon the other to provide the desired length for the overall column that may be deemed necessary to attain effective and efficient chromatography. Obviously it depends upon the mobile phase being subjected to chromatography, and the type of packing provided within the column that controls and determines the length of column necessary, and whether or not even shorter columns may be employed.

SUMMARY OF THE INVENTION

This invention contemplates the assembly of a column for use in particularly preparative chromatography, generally, as previously briefly aluded to, columns that may be assembled together to form a modularly constructed assembly for use in chromatography. This invention is devised as a system for resolving the type of problems that have rather plagued the art of chromatography, so that now through this development various styles of modular columns, having differing internal diameters, can be conveniently connected together, mounted one upon the other, and to that length which is deemed necessary and sufficient to provide for the type of effective chromatography considered necessary for the mobile phase being treated. The invention is characterized by utilizing modular columns having flanged ends used for joining sections of these columns together in order to change the length and to increase and/or decrease the internal diameter of the column to achieve optimum separation. The modular units or individual sections of columns are connected together by using modular adaptors between the column sections which make the ability to add sections together quite a facile performance. Through the use of various of types of frits, generaly fabricated of the sintering process, as known in the art, arranged between the column sections, dissipates excessive build up of pressure and thus avoiding the collapse of the fragile stationary support media, such as the column packing arranged within each column section. The columns are modular and through the usage of its adaptors are interchangable within the assembled structure. By using sealing means such as O-rings, attaching means such as bolts and/screws, the various modular adaptors, and the plugs, and end caps, the system maintains structural integrity that may be subjected to significantly high internal pressures as reguired for performance of effective chromatography. In addition to the modular adaptor for use with columns of the same internal diameter, as envisioned for this invention, what is identified as a cone adapter may be used to attach columns of differing internal diameters, particularly of diameters of that type just previously explained with respect to whether a semi-preparative, preparative, or process liquid chromatography may be required. And, such a cone adapter may be used to attach these columns of different diameters together, in addition, such an adapter can also be used with a slurry packing instrument when the packing material for a column is initially prepared. In addition, the cone adapter can be used with what is identified as a guard column, which generally is that type of a short column body that may be affixed directly to the assembled column, generally at the entrance portion of the overall column assembly. In this manner the chromatographer can optimize preparative HPLC by coupling columns of varying lengths, differing internal diameters, as through the usage of select adapters, as described herein.

The present invention possesses the following improvements and characteristics, primarily useful in preparative HPLC.

1. It avoids the necessity of the technician having to buy a wide variety of column lengths and internal diametered columns to accommodate all types of separations.

2. It allows modular sections of columns of varying lengths and internal diameters to be used as modular units together, to form columns of varying lengths and internal diameters;

3. The column lengths may be expanded to fit any type separation required by the circumstances;

4. A modular adapter allows the stacking of column sections to change the overall column length;

5. A porous frit, with or without handles, which separates and/or supports the stationary column packing material, thereby preventing the collapse of the column support media.

6. Tubing connectors associated with end or cover plates for accommodating feed tubing of differing diameters.

7. The porous frits incorporating stem means for use for ease of handling of the frits during their application or removal.

8. Column end plates or lids, generally two types envisioned, one of which is totally flat for reduced end void, while the other incorporates a shallow funnel to provide for convenient dissemination of the mobile phase during its transfer during during the performance of chromatography.

9. The various modular sections that may be used in high pressure liquid chromatography such as when joined together by suitable attaching means in order to form an overall column for obtaining the desired chromatorgraphic results as required under the circumstances.

10. Cone adapters for connecting column units of different internal diameters together, are for use as the first and/or last column unit to effectively "funnel in" or "funnel out" the mobile phase.

11. Annulus frits used with tap means adaptors.

12. All components are generally inert to the liquid system introduced.

13. All modular units and components are complimentary in fitting with respect to each other in order to provide for their tight seal into an overall chromatographic column.

BRIEF DESCRIPTION OF THE DRAWINGS

This invention is illustrated by the following Figures wherein:

FIG. 5 is a longitudinal cross section of FIGS. 2 and 3;

FIG. 6 is an end view of the end of the guard column of FIG. 5 without the end plate, as seen along the line 6—6 of FIG. 5.

FIG. 7 is an end view of the modular adapter, as seen along the line 7—7 of FIG. 5;

FIG. 8 is a cross-sectional view of the modular adapter of FIG. 7;

FIG. 26 is a perspective view of an assembly of this invention showing the end plate, unit column section, adapter with tap means, another unit column section, a cone adapter, smaller internal diameter unit section, regular adapter, another smaller internal diameter unit section, column end cone adapter, and another end plate;

FIG. 27 is a longitudinal cross section of FIG. 26.

Generally, the more essential components of this invention are listed as follows:
1. Column Body and Main Column
2. Flange
3. Lid or End Plate
3a. Lid Funnel Shape
4. Tubing
5. Male Tubing Connector
6. Screws and/or Bolts and Nuts
7. Guard Column
8. Large 0-Ring
9. Small 0-Ring
10. Porous Frit
11. Porous Frit Stem
12. Modular Adapter
13. Cone Adaptor
14. Funnel-like Cone shape in Cone Adapter
15. Adapter with Tap Means
16. Tap Hole in Tap Adapter
17. Tap Means such as Spigot
18. Annulus (Donut) Frit Used with Tap Adapter.

DESCRIPTION OF THE PREFERRED EMBODIMENT

Figure 1:
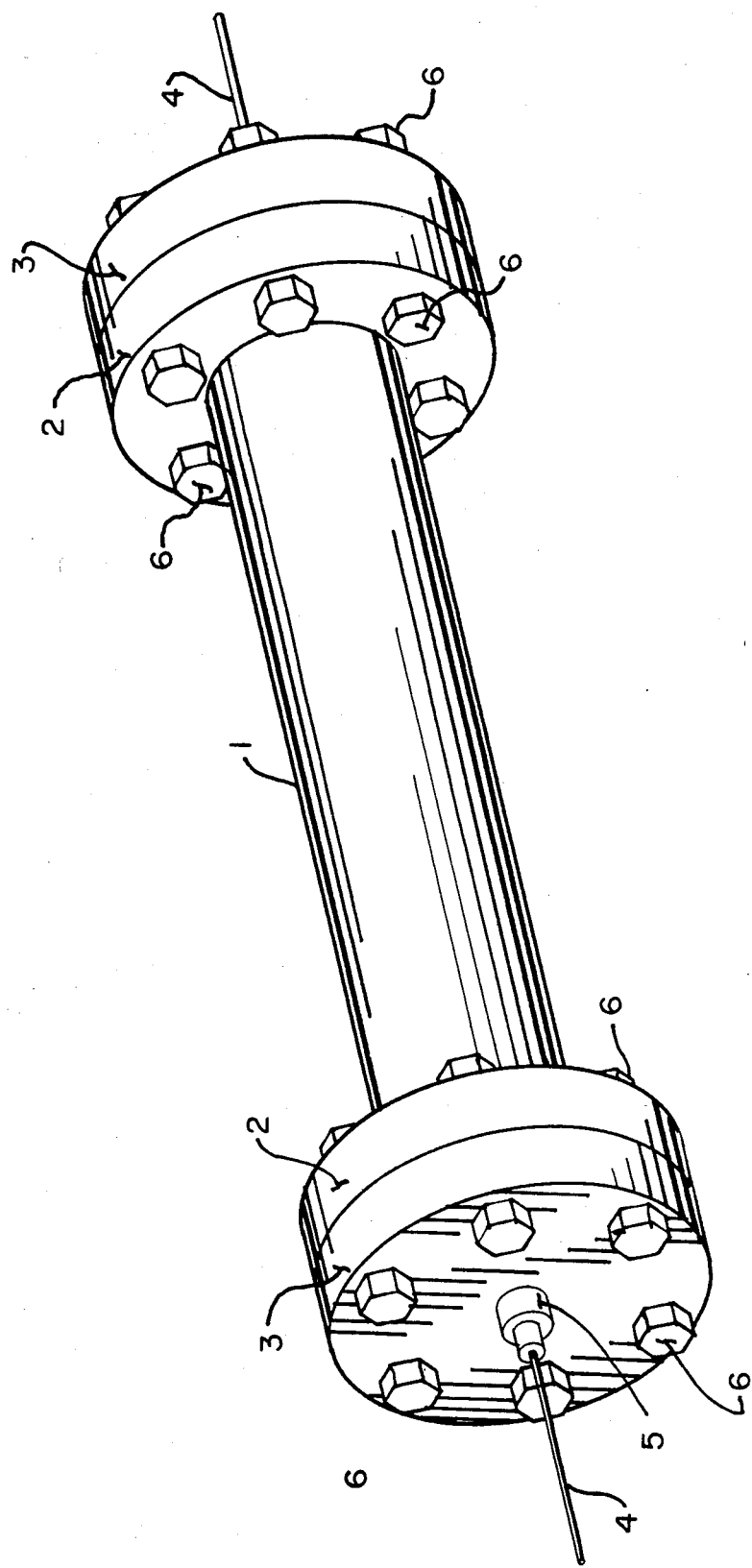
FIG. 1 is a perspective view of an embodiment of this invention, showing a chromatographic column with end plates.

The basic high pressure liquid chromatographic unit is shown in FIG. 1 where 1 is a chromatographic column section, having integral or threadedly secured flanges 2, upon which the end plates or lids 3 are attached to the flanges by means of screws and/or bolts and nuts 6, to provide a tightly secured, and high pressure chromatography system. On each of the end plates is a male tubing adapter or connector 5 to which tubing 4 is attached and by means of which liquid enters the system on one end and the separated liquid exits at the other.

One modular embodiment is shown in FIGS. 2 through 9. The components of this modular embodiment are presented in FIG. 9, which shows the following components in sequence from left to right:
Tubing 4
Male Tubing Connector 5 (liquid entrance)
End Plate 3
Large O-Rings 8
Small O-Rings 9
Porous Frit 10

Porous Frit Stem 11
Guard Column with Built-in Flange 7
Large O-Rings 8
Section Modular Adapter 12
Chromatographic Column Section 1 with Terminal Flanges 2
Porous Frit or Disks (without stem) 10
Large O-Ring 8
Small O-Ring 9
Lid or End Plate 3
Tubing (liquid exit) 4

Figure 2:
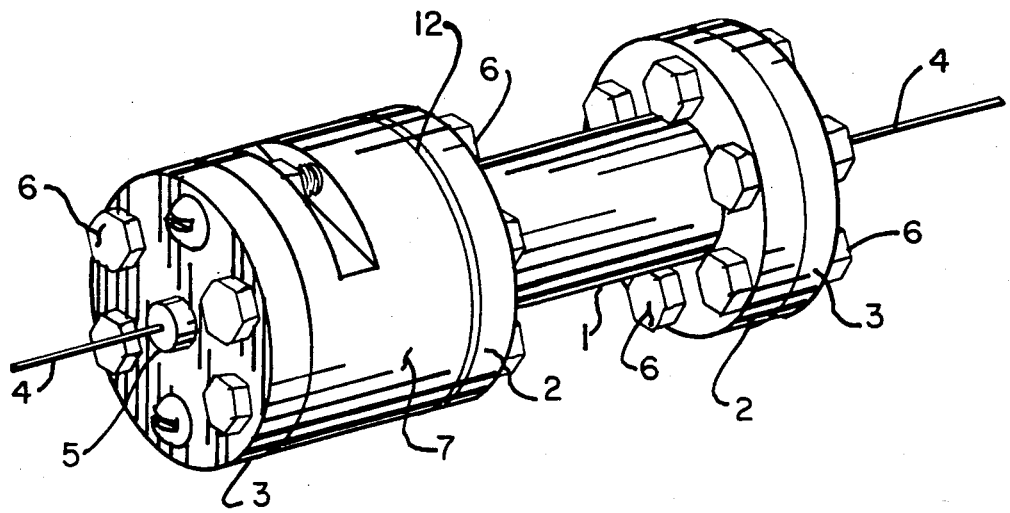
FIG. 2 is a perspective view of an embodiment of this invention showing a guard column, a unit column, and end plates.
Figure 3:
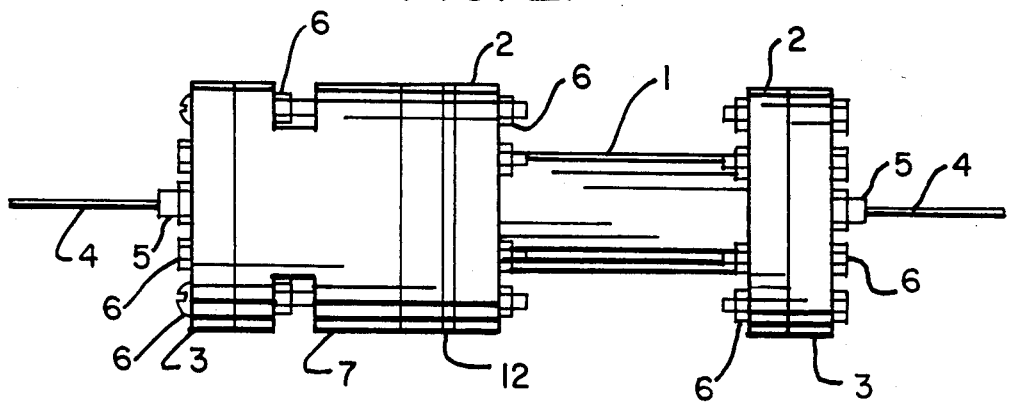
FIG. 3 is a side view of FIG. 2.
Figure 4:
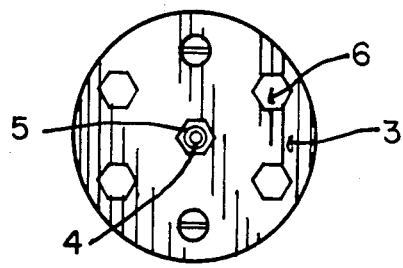
FIG. 4 is an end view of FIG. 3, showing an end view of the end plate.

All of the above components as identified above are bolted together to yield a high pressure unit as shown in perspective in FIG. 2, and from its side view as shown in FIG. 3. The entrance and exit views for this particular embodiment can also be seen from FIGS. 2 and 3, as also disclosed in FIG. 4, which provides a front end view of the assembled device. It might be commented herein that the high pressure liquid chromatography unit of this invention, as shown in this particular embodiment, may have internal diameter dimensions that may vary between a fraction of an inch, up to more than 6 inches in diameter, as previously explained. Normally, in high pressure units, pressures for the smaller diametered columns may attain a psi in the range of 2000 or more, whereas, when the internal diameter for the device may be in the range of 5 to 6 inches in diameter, pressures generated and exerted internally within such columns of that particular design may be more customarily within in the range of 100 to 200 psi.

As shown in these particular drawings, and in particular in the cross-sectional view displayed in FIG. 5, the column unit 1 has threadedly engaged to each of its ends the flanges 2, with the front end flange 2 having secured to it the guard column 7, and arranging intermediate it and the proximate flange 2 the section modular adapter 12, as can be noted. The end plates 3 are secured at each end, by means of the disclosed bolts 6, which are rigidly tightened in place through their connection with the disclosed nuts 6. Securing within the front end plate or lid 3 is the male tubing adapter 5, which has the incoming liquid conveyed through it by way of the tubing or conduit 4, as noted. Upon entering the column, the liquid encounters the porous frit 10, and then is conveyed under pressure through the porous solid packing material F packed within the column 1, and its guard column 7. The processed liquid passes through the column, attains the desired separation sought for by the chromatographic unit, as previously explained, and then exits through the outlet end frit 10, before passage through the outlet tubing and tubing connector 5, as noted at the right end of the apparatus.

Figure 9:
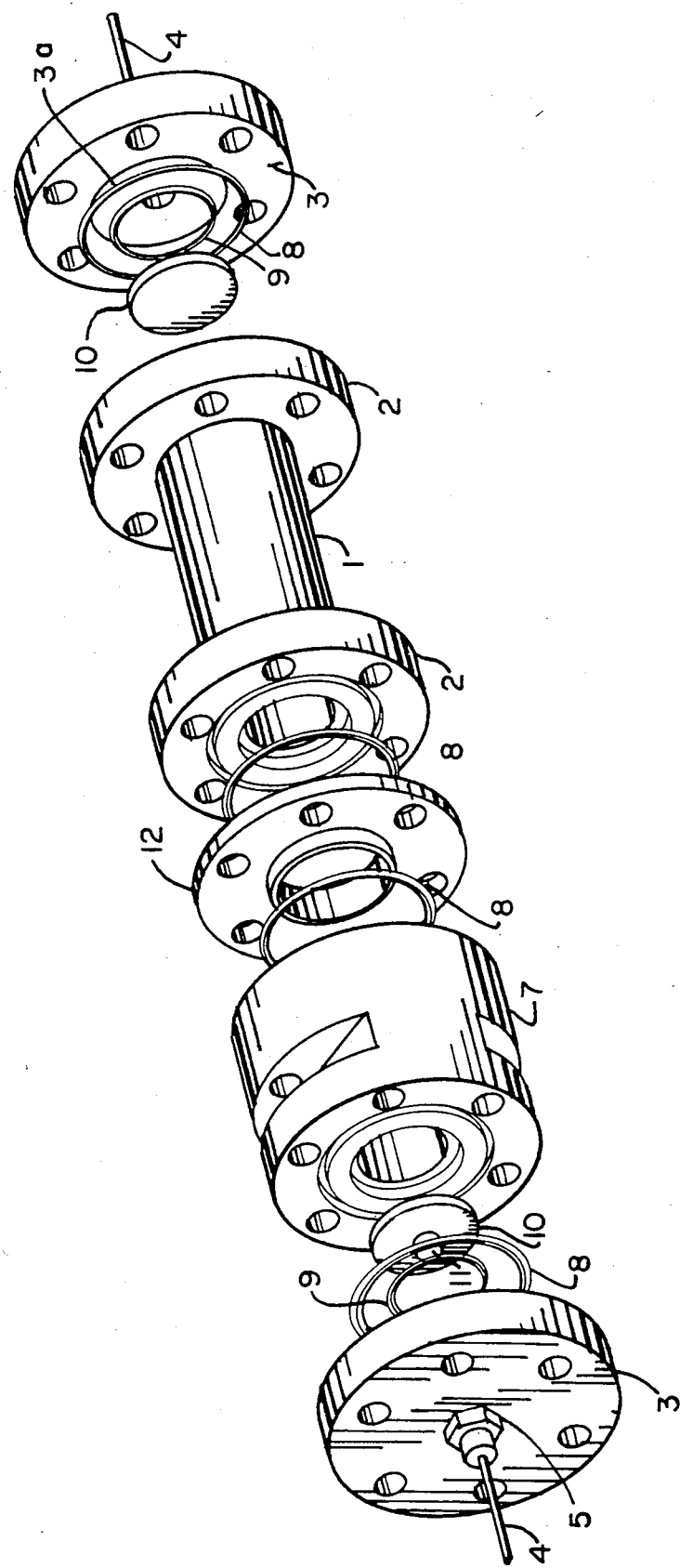
FIG. 9 is a perspective exploded view of FIG. 2, showing the component parts used in its assembly.

As previously stated, all of the various components as just explained are secured together into a contained embodiment, incorporating the various components as shown in the exploded diagram as disclosed in FIG. 9, to form the type of unit as can be seen in FIGS. 2 through 5. And, an end view of the unit, as disclosed in FIG. 6, and taken along that line 6—6 of FIG. 5, shows the inlet end of the guard column 7. In addition, FIGS. 7 and 8, as taken along line 7—7 of FIG. 5, shows the modular section adapter 12, both in an end view, and in a sectional view, as disclosed in said FIG. 8. As can be seen, the internal surface of the modular section adapter 12 is designed with a short sleeve like means, as at 12a, and cooperates with the proximate flange 2 and the proximate guard column in order to provide a smooth interior structural wall thereat, to enhance usage of the column when subjected to the type of pressures as previously explained, and when liquid flows therethrough.

The component parts of the end-to-end connection of a pair of modular sections include a pair of flanges 2, the modular section adapter 12, with O-rings and frit, as shown in perspective view in FIG. 10, where (from left to right) these components are as follows:

1st Chromatographic Column Section 1
Flange of first Chromatographic Column Section 2
Large O-Ring 8
Pourous Frit 10
Modular Adapter 12
Large O-Ring 8
Flange of the 2nd Chromatographic Column Section 2
2nd Chromatographic Column Section 1

Figure 10:
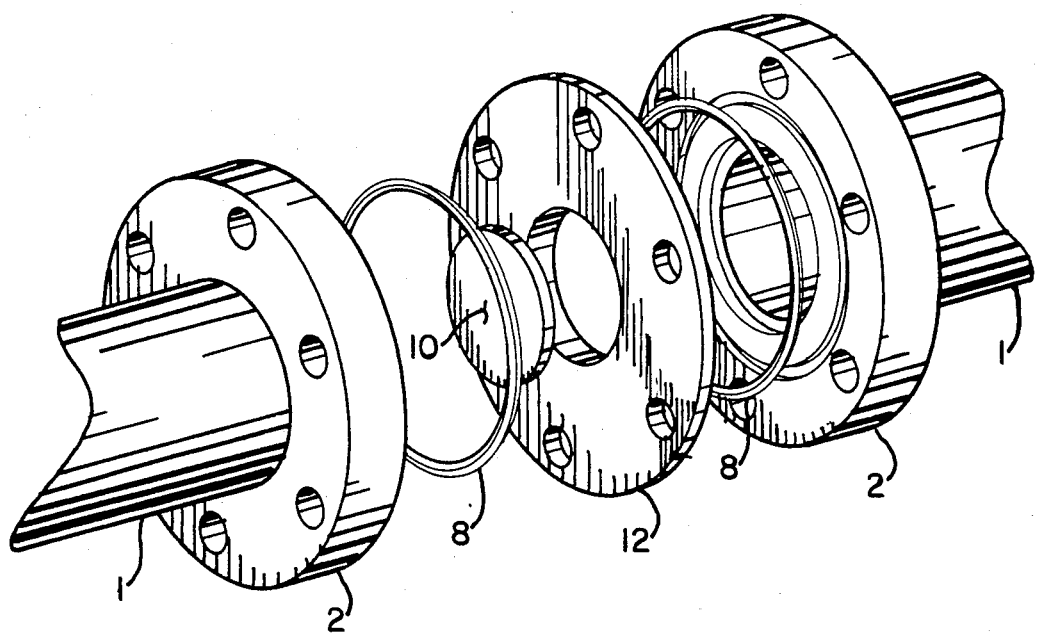
FIG. 10 is a perspective exploded view of the component parts used in joining two modular sections and employing a modular adapter.
Figure 11:
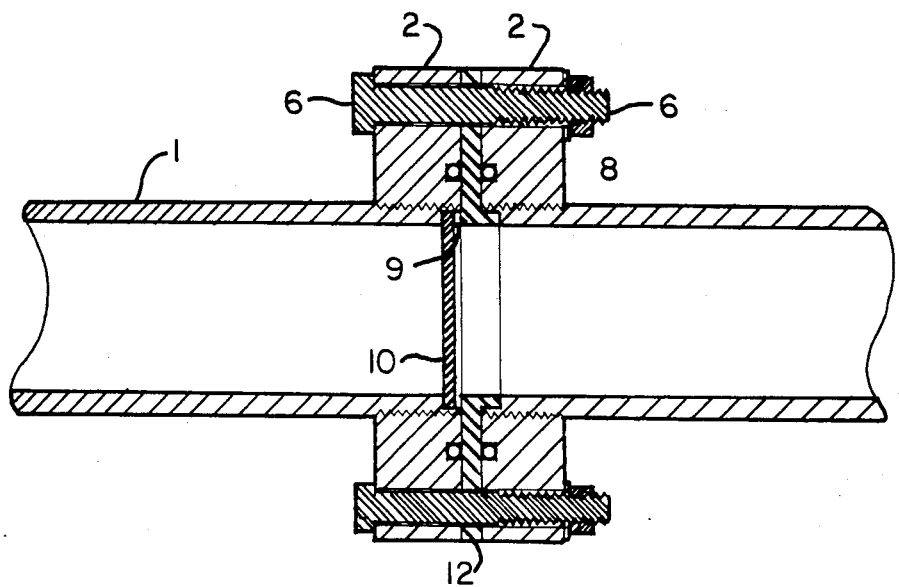
FIG. 11 is a cross sectional view of FIG. 10 when assembled.

A longitudinal cross section of the bolted together assembly of FIG. 10 is shown in FIG. 11.

Figure 12:
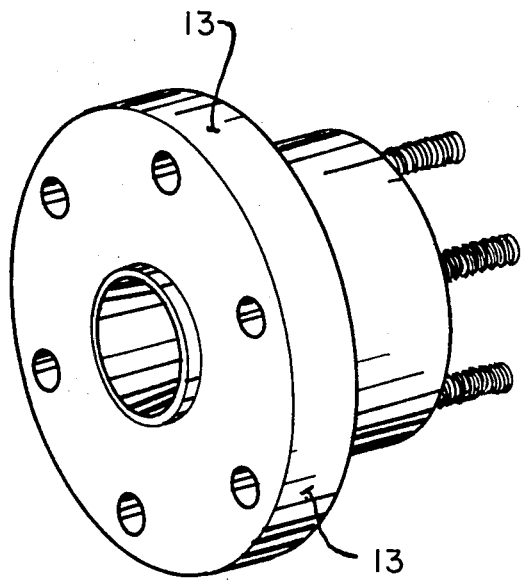
FIG. 12 is a perspective view of a cone adapter.
Figure 13:
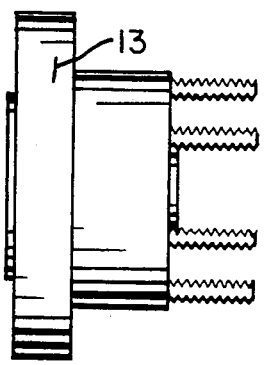
FIG. 13 is a side view of FIG. 12.

The cone adapter which is used to join modular chromatographic column sections of different internal diameters together is shown in perspective in FIG. 12, and in side view in FIG. 13.

Figure 14:
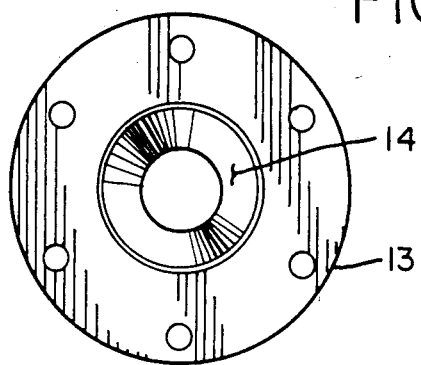
FIG. 14 is a view of one end of FIG. 13.
Figure 15:
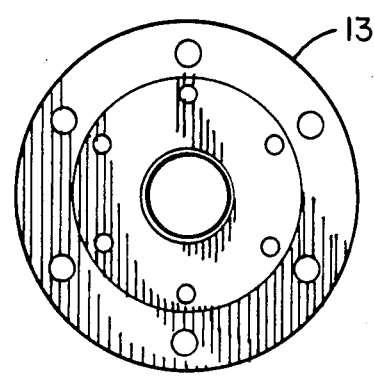
FIG. 15 is a view of the other end of FIG. 13.

FIG. 14 shows end view from the left end of FIG. 13.
FIG. 15 shows the right end view of FIG. 13.

Figure 16:
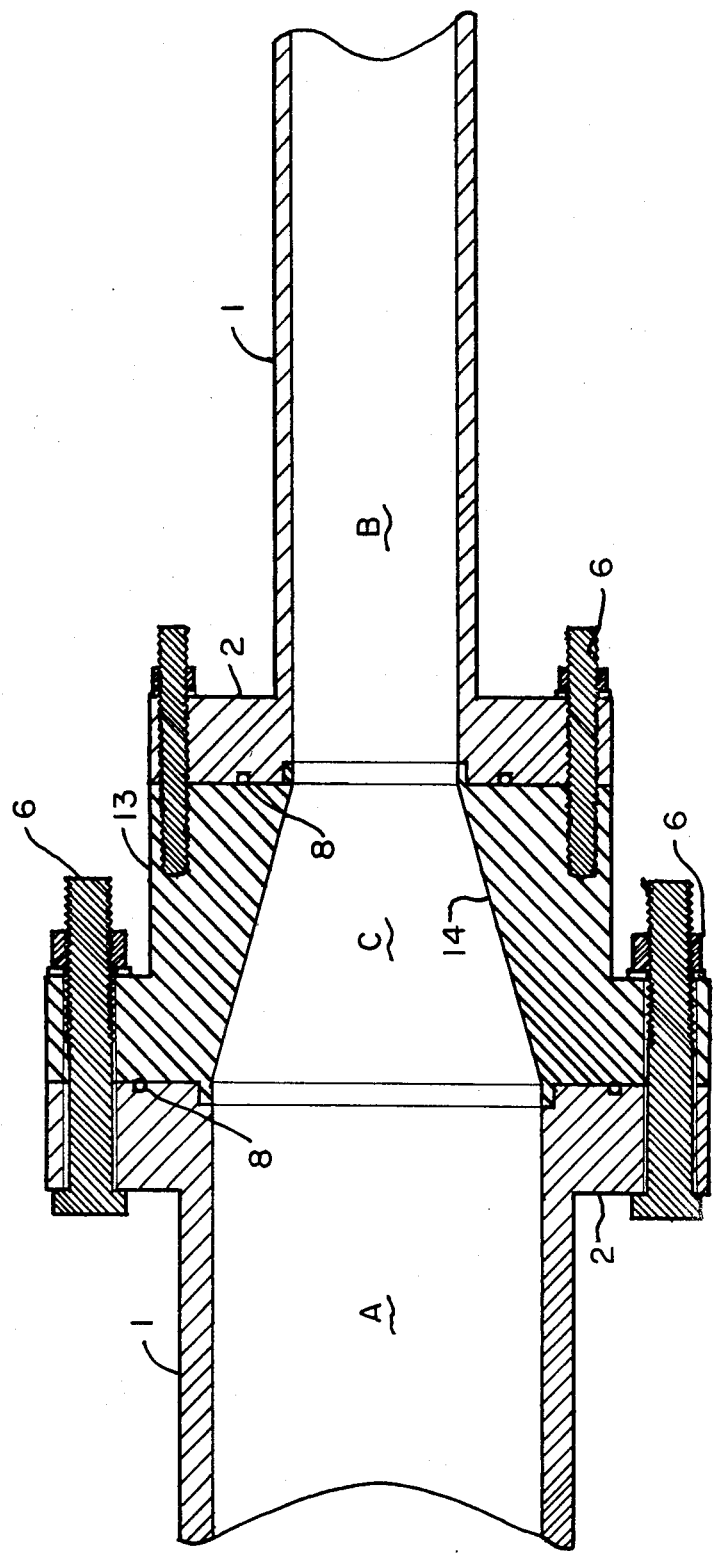
FIG. 16 is a longitudinal cross sectional view of the cone adapter attached to column sections of differing internal diameters.

The use of the cone adapter in joining chromatographic column sections of different internal diameters (intermediate column adapter) is shown in longitudinal cross-section in FIG. 16, where the wider column section A is "coned-down to" the narrower column section B by means of the cone adapter C.

The cone adapter can be used as a chromatographic end column, such as a general column, in contrast to joining two column sections intermediately together as of differing internal diameters. For this type of embodiment, the component parts of this assembly are shown in perspective in FIG. 19, and include the following components from left to right.

The end plate or lid 3 having the inlet tubing 4 securing with the male tubing adapter or connector 5 forms the liquid entrance through the said lid. An O-ring 8 is designed for snug seating within the groove 8a of the adapter 12, and disposed within its aperture 10a is the porous frit 10, which is held in position be means of O-ring 9. The frit is accommodated within the aperture 10a, and cooperates with the integral extending sleeve like portion 13a of the cone adapter 13, and the O-ring 9, for securement in place when assembled. Another O-ring 8 fits within a groove (not shown) provided upon the opposite surface of the adapter 12, for providing a tight seal against the surface 13b of the said cone adapter 13. In addition, when these various components are secured together, the bolts 13c provide for their tight binding into sealed closure so as to prevent the escape of any pressurized liquid generated within the column 1, as during the high pressure functioning of the chromatographic unit.

Figure 17:
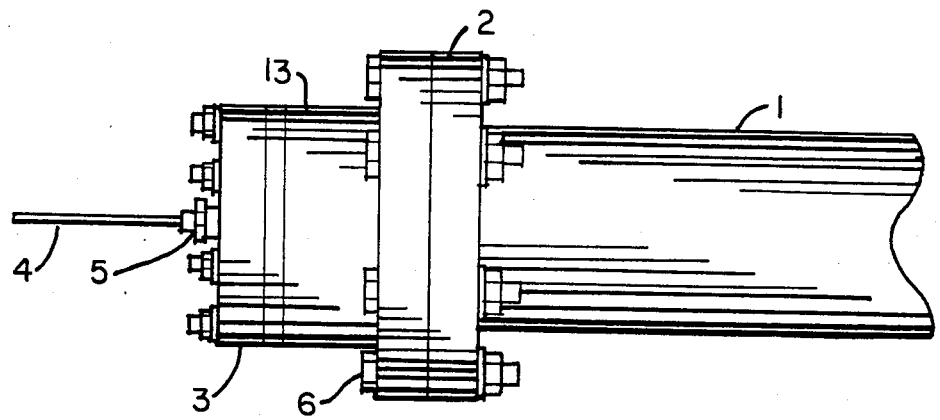
FIG. 17 is a side view of the cone adapter used as a general column attached to a section or main column.
Figure 18:
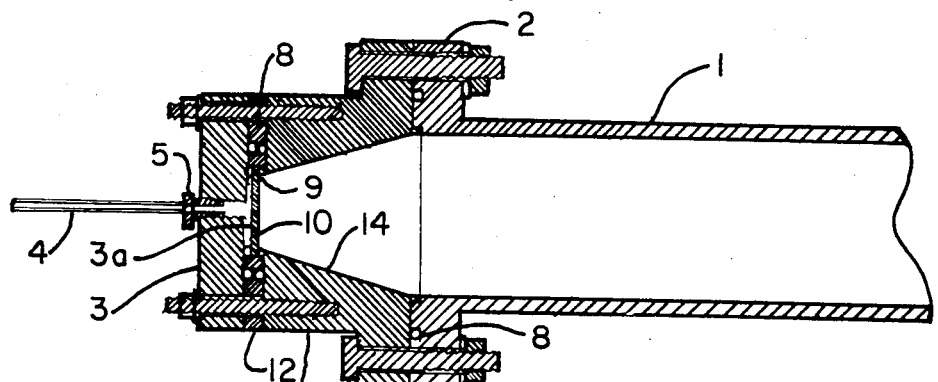
FIG. 18 is a longitudinal cross section of FIG. 17.
Figure 19:
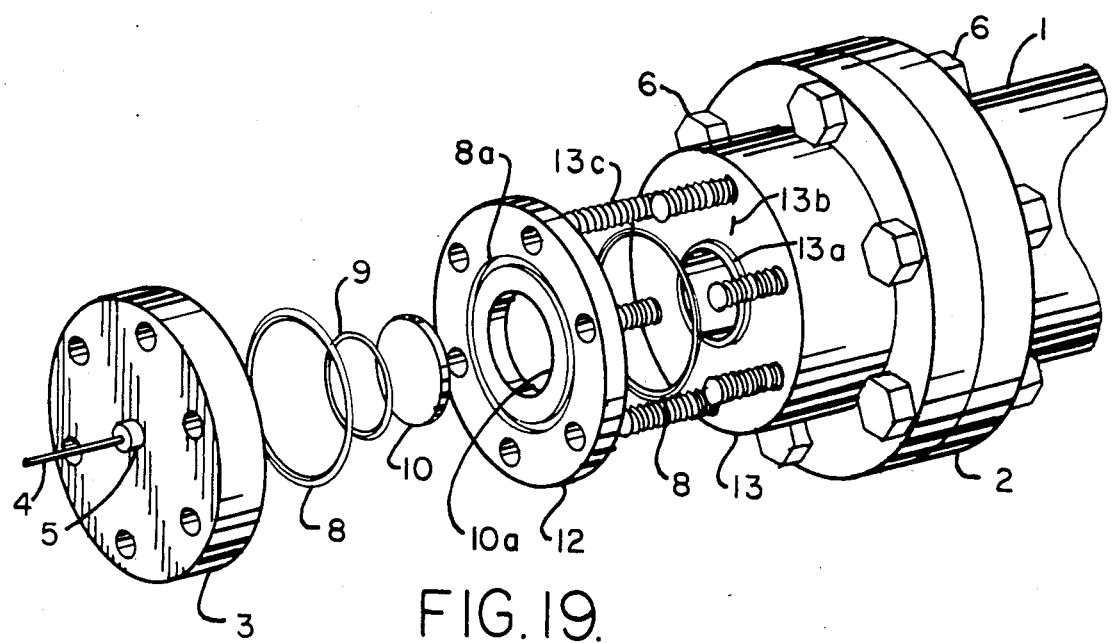
FIG. 19 is an exploded perspective view of the components assembled in FIG. 17 and 18.

A side view of FIG. 19 assembled and bolted is shown in said FIG. 17, and a longitudinal cross section thereof is shown in the FIG. 18.

The cone adapter on the end of the column may be used as a guard column and as a device which disperses the loading liquid more uniformly for better separation. It may also be used at the exit end of the columns for funnelling the eluted liquid.

Figures 20, 21, 22:
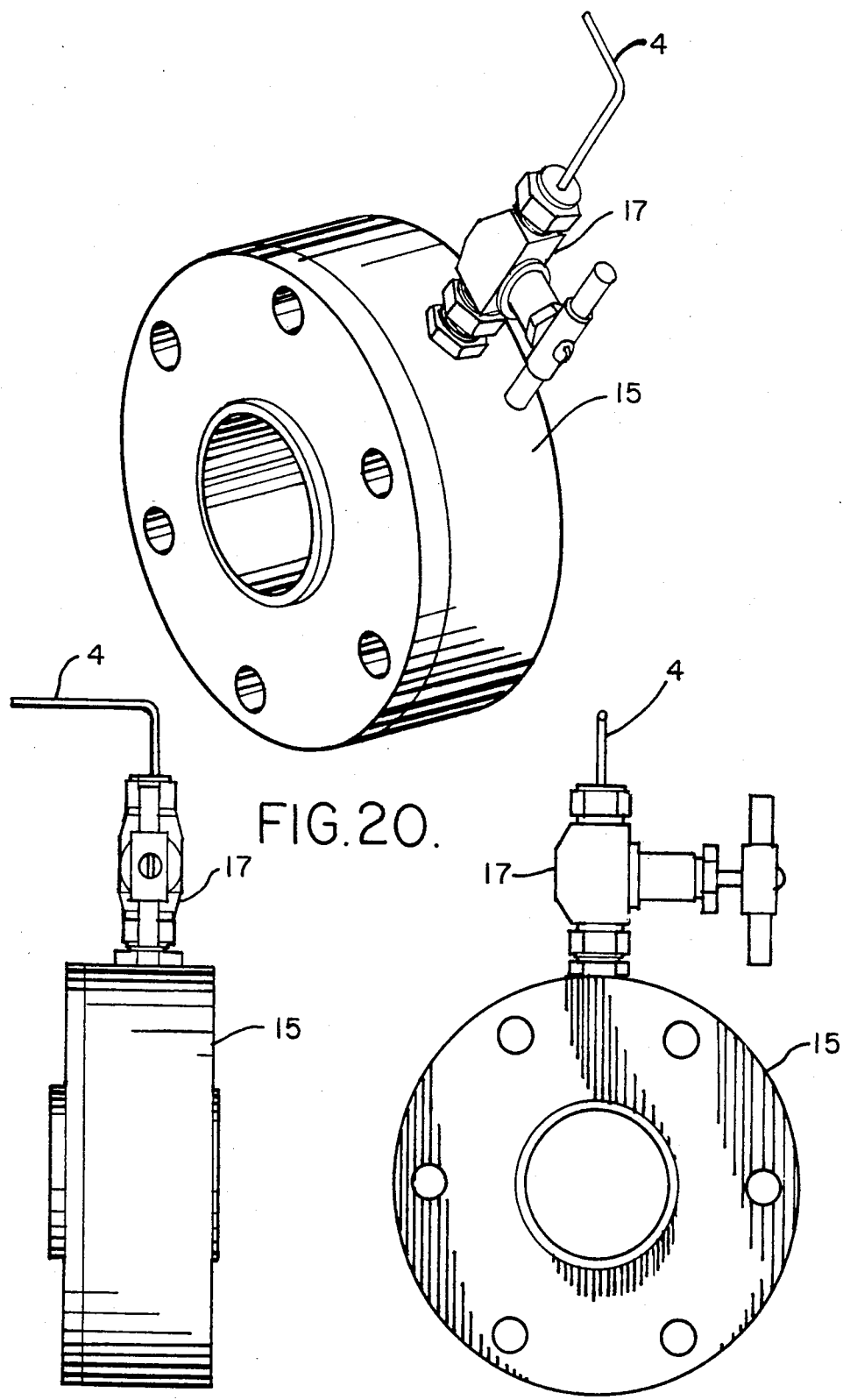
FIG. 20 is a perspective view of the adapter with tap means.
FIG. 21 is a side view of FIG. 20.
FIG. 22 is a frontal view of FIGS. 20 and 21.

The adapter means with tap means (the tap adapter) is shown in persepctive in FIG. 20, in side view in FIG. 21, and in end view in FIG. 22, and not only enables the connection of two modular chromatographic column sections together but also has a tap means which (in conjunction with an annulus frit) enables the liquid to be bled off before it enters the next column. The additional features of the tap means includes its usefulness in selecting the portions and fractions of the mixture which will enter the next column section without contaminating it with unwanted chemicals.

Another application of the tap adapter allows starting with one type of liquid mobile phase, and then through usage of the tap, introducing another liquid mobile phase therein. This allows pre-purification of the sample in the column itself.

Figure 23:
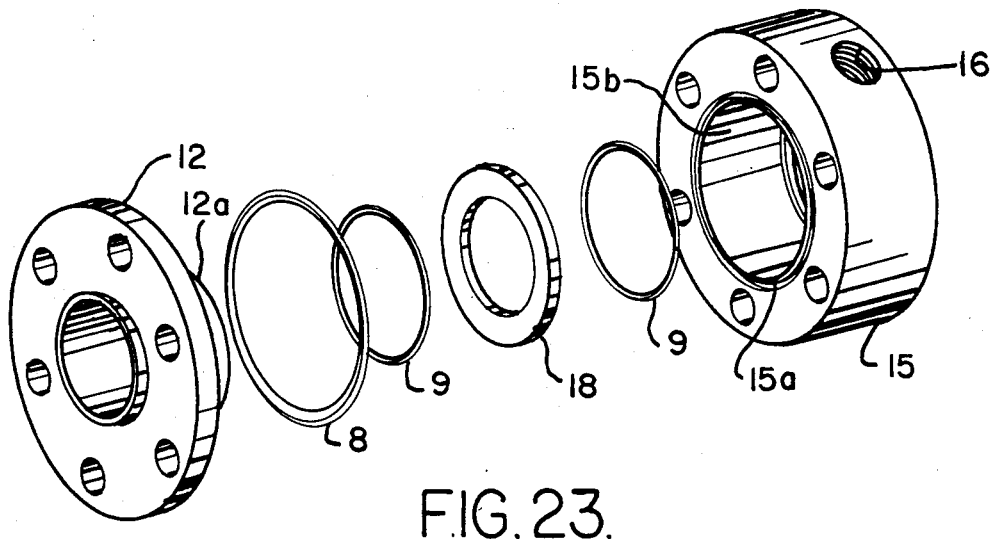
FIG. 23 is a perspective exploded view of the adapter with tap means of FIG. 20, showing its individual components.
Figure 24:
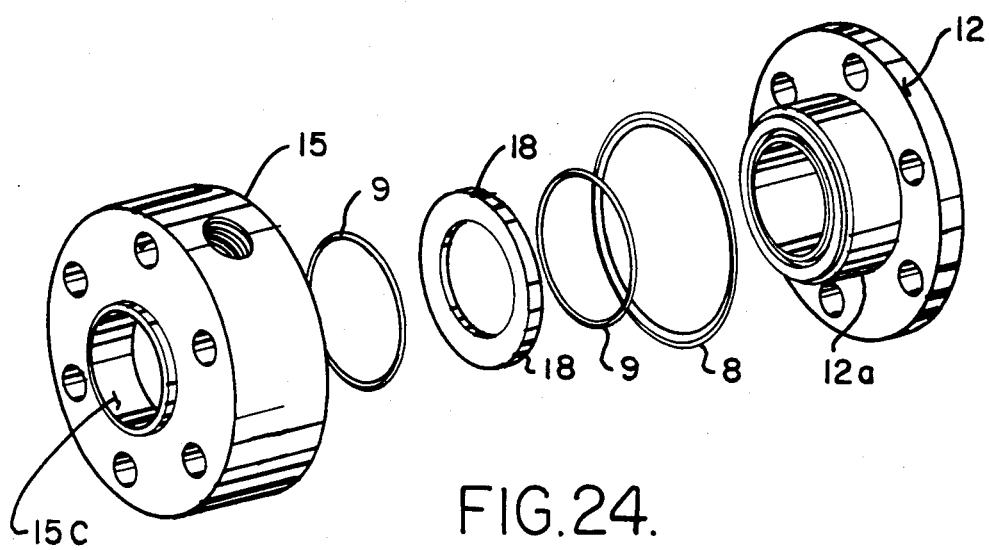
FIG. 24 is a perspective exploded view of the adapter with tap means of FIG. 20, with the components being shown in a view opposite upon that of FIG. 23.
Figure 25:
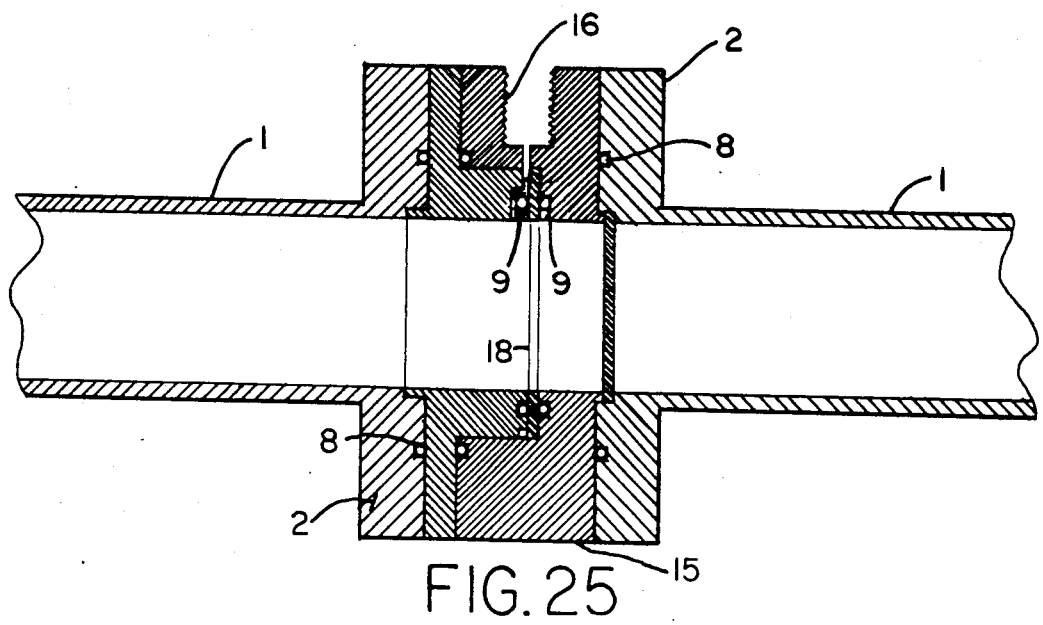
FIG. 25 is a longitudinal cross sectional view of the adapter with tap means joining two unit modular column sections together.

The component parts used in the assembly of the tap adapter are shown in perspective in FIG. 23. As can be seen, a modular adapter 12 is provided for connection with the tap adapter 15. A large O-ring 8 is designed for securing between these two adapters and generally seats within a peripheral groove, as at 15a, provided at the entrance into the formed aperture 15b, as disclosed. An annulus formed frit 18 locates within the aperture 15b, and a pair of O-rings 9 are disposed for seating adjacent each of its sides. An integral sleeve, as at 12a, is formed with the modular adapter 12, and it inserts within the aperture 15b for compressing tightly against the frit 18, in addition to the two O-rings 9. A flange 15c is formed integrally at the inward end of the aperture 15b, and compresses against the frit 18 from its opposite side. As previously explained, FIG. 23 shows the component parts in perspective view from one angle, while FIG. 24 shows the same component parts in perspective view from an approximate opposite angle. And as can be seen in FIG. 25, the tap adapter is shown in its longitudinal cross section, where two chromatographic column sections 1 are joined together with the tap adapter being arranged intermediate thereof. And, as can be noted, the tapping occurs through the installation of the tap 17 within the threaded opening 16, which provides for access into the interior of the unit section 1.

An assembled system is shown in FIG. 26 and 27, and which combines many features of this invention as follows:

Starting from the left end, the lid 3 with male tubing adapter 5 and tubing 4 joins with the flange 2 for the first column section 1. A porous frit 10 is located at the column entrance, interiorly thereof, for purposes as have been previously described. This unit shows a series of four column sections 1, having their various flanges 2 either integrally or threadedly engaged thereon. A tap adapter 15 is provided between the first two column sections, as depicted at the left side of the FIG. 27, while a cone adapter 13 is arranged intermediate the second and third column sections 1, and which adapter reduces the internal diameter of the sections as noted at A, down to the internal diameter B of the next adjacent column section 1, with the internal diameter narrowing as at C formed integrally within the interior of the said cone adapter 13. And, as can be noted, at the right end of the unit, as shown in FIG. 27, another cone adapter 13 may be provided, having a modular adapter 12 provided therewith, before the connection of the end plate 3 thereon, with its associated tubing adapter 5 and the outlet tubing 4.

Figure 28:
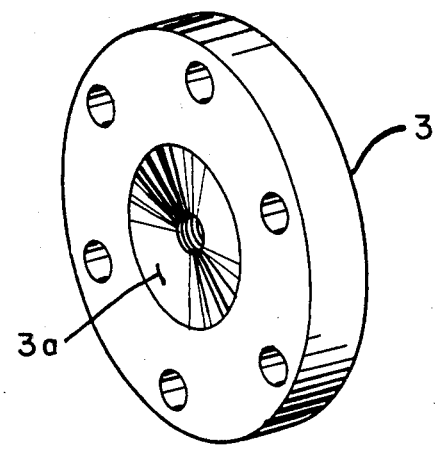
FIG. 28 is a perspective view of an end plate or lid.
Figure 29:
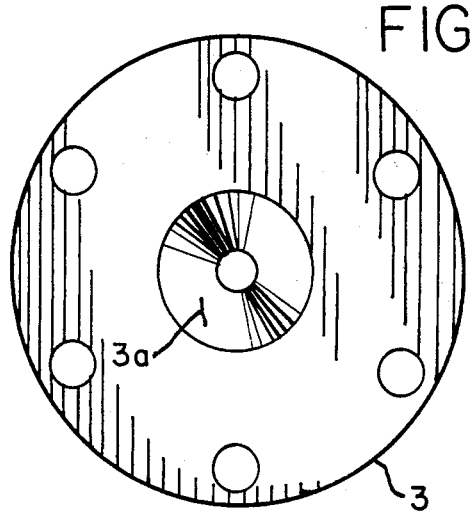
FIG. 29 is an end view of the inside of the end plate.

FIG. 28 shows the end plate or lid in perspective. An inside view of the lid is shown in FIG. 29, showing its shallow funnel shape 3a in the center which spreads the charge of liquid into the column section upon its entering, and funnels the eluted liquid to the center of the column as it exits therefrom.

Figure 30:
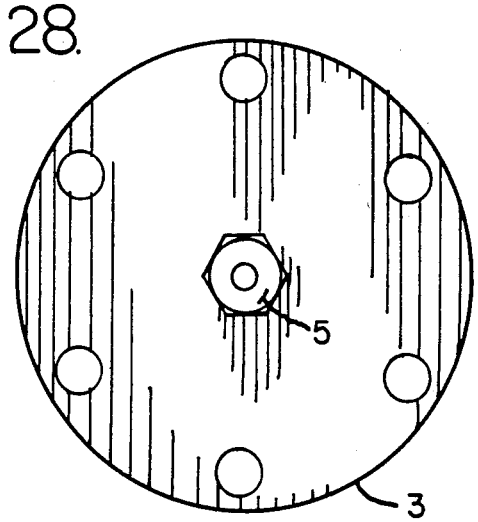
FIG. 30 is an end view of the outside of the end plate.

FIG. 30 shows outside of the end plate to which the male tubing 5 is connected.

Figure 31:
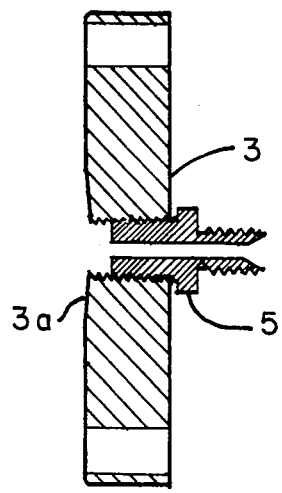
FIG. 31 is longitudinal cross sectional view of the end plate with attached male tubing adapter.

FIG. 31 shows a longitudinal cross section of the end plate as just defined.

Figure 32:
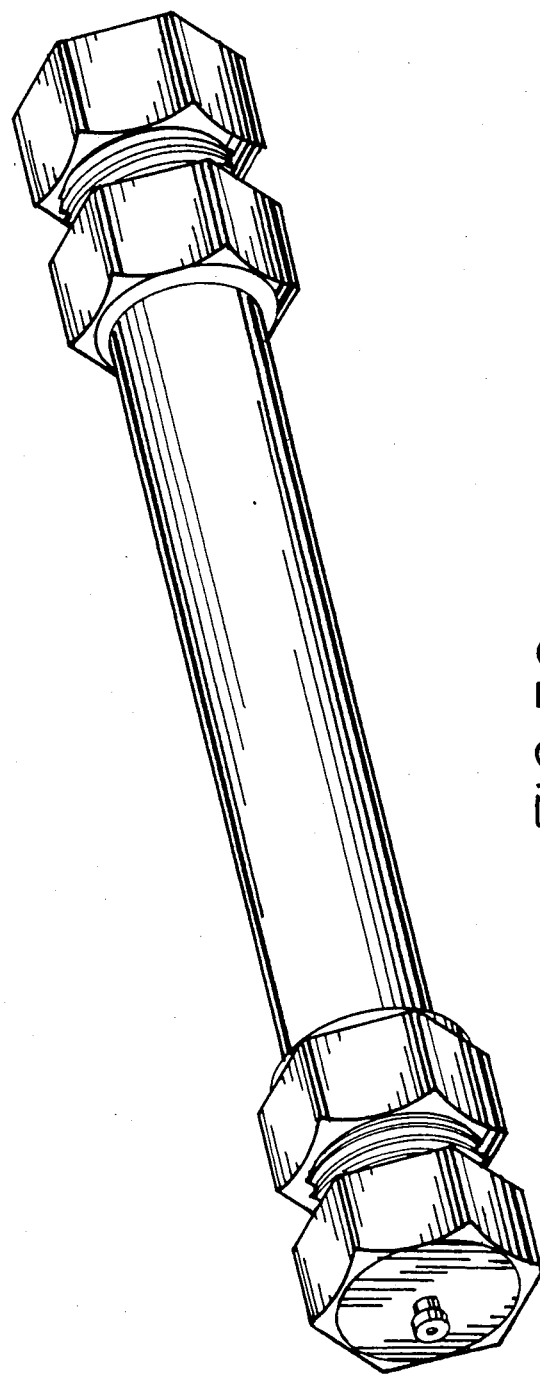
FIG. 32 is a perspective view of an embodiment of the prior art where a column has threaded collars at each end rather than the flange-like means of the current invention.

FIG. 32 shows an example of the prior art with assembly modularity, but without the benefits through usage of the various adapters, flange means, and tap means of this invention.

The simplicity of the present invention allows chromatographic columns to be assembled and disassembled more easily than the screw-type assembly of the prior art as shown in FIG. 32, in contrast to the flange-like means assembly of this invention. The short column section or the guard column, in general, is preferably 5-10 cm in length, for example, as shown in FIGS. 2 and 3, and in cross section in FIG. 5. In the process of chromatography, when using a standard preparative column (such as 25-30 cm column) the top or entrance column is the first to be contaminated, if used by itself, and in many instances may even become clogged. Usually it is preferred to have a short column section (a guard column) in front of the main column section to absorb those contaminations, such as shown in FIG. 5. This approach may avoid contamination of the main column.

By connecting a guard column 7 to the column section 1 with tubing, mixing may occur which impairs the resolution. However, by being able to stack a short column section on top of the main column section (for example, as shown in FIGS. 2, 3 and 5) with the same internal diameter and with the aid of a modular adapter 12, as in FIGS. 2 and 3, and FIGS. 7 and 8, one eliminates the need for the interconnection of the columns with tubing. This is a guard column with the same interior diameter with an extended stacked column section, rather than necessitating two separate columns attaching together.

In addition, the simplicity with which the modular HPLC columns, or Sections, of this invention are assembled and disassembled has an advantage over the conventional prior art columns, as exemplified by the screw-type columns shown in FIG. 32, where column support packing often gets into the threads as previously explained. In addition, cleaning of the frits is difficult, and the washers and frits are difficult to handle in these prior type of devices.

These short guard columns, for example, such as of 5-10 cm, can also serve as an important research tool which enables one to establish the amount of theoretical plates (units of separation) desired to be achieved in optimizing the conditions in regard to the column size (i.e. length and/or width) and column support (i.e. stationary packing phase) and mobile phase (the solvent system) for a particular separation. A 5 cm or a 10 cm length modular HPLC column section may be used as a yard stick in the trial of a certain separation where one adds on top, or on the bottom, as many unit guard columns as are needed since the column sections have the same units on both sides and are totally modular. Moreover, in scaling up a purification-production or HPLC-preparative work system, the short and wide internal diameter column section is more appropriate to the actual preparative conditions. The conditions obtained from an analytical column, which is the most common type column in practice today, does not provide the accurate results that a short and wide column can obtain. This may be due to wall effects, etc., which is encountered with an analytical column.

In many cases separation may be carried out on the very top of the column such as is the case with ion-exchange chromatography. In this case a short column would be sufficient and more advantageous than a long column. Moreover, in many cases such as in the chromatography of the proteins, an excessive lengthy column (30 or 50 cm) is to the disadvantage to the chromatographer since the compound to be purified may be impeded in the column and recovery of the pure product may suffer.

In addition, the short and wide diameter column is ideal for the promotion of a high flow rate with less back-pressure when pressure is imposed on the column, all which leads to a savings in time, solvents, and so forth. Furthermore, there is an additional advantage in that it is easier to change the column support medium in a short and wide column than in a long and narrow column.

In addition, a short column (5–10 cm slurry packed with 10 micron particles) often provides enough plates for a particular separation initially that one can eventually find worth using the usual standard preparative lengthy column (25–30 cm).

We have found that that another advantage of this invention is that the mathematics in calculation of the scale up are easier and more accurate from a semi-preparative or a preparative column than from an analytical column.

The trend today in preparative HPLC, is to utilize a smaller particles size (15–10 micron) packing medium which in turn produces higher back pressures. In many cases the available solvent delivery systems may not have those capacities. By shortening the standard preparative column and by using a short and wide diameter column, as of this invention, one obtains less back pressure and thus more favorable conditions.

Since the manufacturers of fine, more sophisticated, and high purity chemicals in biotechnology, pharmacology and other chemical industries resort more often to preparative HPLC, the use of modular columns is an enhanced addition and a great asset to those industries.

A modular HPLC column is assembled, as in FIG. 5, from the following parts: The column body section 1, and the guard column 7, held together through an adapter and screw means. The column section is in essence a length of metal tubing, with the flanges 2 and the lid or end plates 3 at the entrance and exit ends. The bolts and screws 6 tighten the lids to the column section, or more precisely to its flanges. The frits 10 which are usually made of a porous stainless steel, and are used adjacent the entrance and exit ends of the column, proximate the end plates. The frits actually hold the column support packing medium within the column, and therefore their size of porosity is important, as known in the art. Bigger particles provide less back pressure for the solvents as used in the system. The frits may also have their stems or handles 11 for easy grasping. The small O-rings 9 are placed adjacent the surface of each frit to seal the column. And, in the groove of each flange there is the location for the additional large O-rings which provide some additional sealing, as a safety measure. In the case where a modular adapter 12 is used to connect two modular column sections, only the large O-ring 8 is used, in which case said O-ring is the only seal between the two connected columns. In the center of each end plate there are threads for accommodating the male tubing adapters 5. The tubing 4 in each male tubing adapter 5 connects the column to the solvent delivery system, or its collector.

The modular HPLC columns and all the other parts (except perhaps the bolts and nuts) are preferably made of 316 stainless steel, or related operating materials, such as Hastelloy or Monel, so they may be used with and be resistant to various solvent systems, buffers and mild acids or bases. The 5 cm guard columns with the internal diameters of ½ inch to 1 inch and the 10 cm column sections with the internal diameters of 2 inches to 3 inches are preferably made in one piece of stainless steel, i.e., the flanges and the section body are made in one piece. The larger column sections are preferably made of three different pieces: (1) the column body section (stainless steel pipe), (2) the flanges and (3) the end caps (lids). The lids fit any column with a given internal diameter, whether the column section is made of one piece or from a cylinder and flanges. In the examples, the column flanges are preferably attached to the section with threads, or integrally formed, by Hilard welding. The inside of the modular section is preferably polished or honed to a 30 to 40 microns finish and the end plates are preferably polished to a 32 finish. The end plates, as shown in FIGS. 28 and 29, have a shallow funnel, or depression 11, for example of about a fraction of a degree to 10° slope, to provide for even dispersion and elution of the solute and the eluent. Preferably the lid has in its center a threaded opening for a male tubing adapter 5 to connect, and preferably of 1/16 inch or ⅛ inch, or any standard tubing may be connected therewith according to the user's needs.

The formed modular column of this invention is so designed that they can be used with any conventional HPLC solvent delivery system and/or with any specially designed solvent delivery system, provided that the back-pressure does not exceed the rated pressure of the system. For example, the ½ inch and 1 inch modular HPLC columns of this invention are preferably rated to withstand maximum pressure up to 4000 psi, whereas the 2, 3, 4, 5 and 6 inch columns are preferably rated to 2000 psi maximum pressure, or below. Since the dry packing and slurry packing of the modular columns of this invention are relatively easy, the present invention simplifies these operations.

The modular HPLC columns may be made in various internal diameters and lengths, as previously summarized. In practice, the internal diameters include ½", 1", 2", 3", 4", 5" and 6 inches, or other lengths according to needs, such as, for example, 5, 10, 20, 30, 50 and 100 cm, etc.

The lids are attached to the flanges by simple bolts and/or screws, as previously described.

In many cases the chromatographer would like to use different column supports intermediate each unit column section and yet not interrupt the integrity of the total column. This is done with the modular sections by using the modular adapter and a frit between the unit column sections. For instance, one unit column section can be packed with silica gel coated with $C_8$, and the other unit column may be packed with silica gel coated with $C_{18}$. This type of chromatography is called mixed modes. Another example is to have an ion-exchange column support packing in one unit section, and a molecular sieve type of column support medium in yet another unit column section, and so forth. Thus, a wide selection of diverse packing materials can be employed quite easily in this system and for providing very distinct results.

Another particular case is also worthwhile mentioning. This is in the case where column support packings are sensitive to excessive pressures, such as DEAE cellulose, porous silica gel, etc. These column supports lend themselves perfectly to the sectional unit columns. The use of a frit between these sections will dissipate some of the excess pressure and avoid the collapse of the column support packing.

The modular adapters, which are preferably made of 316 stainless steel and with 32 finish, enables the connection of two modular HPLC columns sections together. In order to make a seal between the adapter and a large section, the large O-rings are inserted in the groove of the body of the column or flange and lid, as shown in FIG. 9. The modular adapter also enables the connection of two modular sections with a frit between them, as disclosed in FIGS. 10 and 11. The modular adapter also enables the connection of two sections with straight ends.

The cone adapters are preferably made of 316 stainless steel and 32 finish. The slope in all of the cone adapters has preferably a 16° slope. But, obviously, other angles of slope may be employed depending upon the adapter size and the conversion diameters. The length of the cone adapter is preferably 5 cm, except for the ½ to 1 inch cone adapter which may be only 2.5 cm.

The inter-column section cone adapter is preferably made of 316 stainless steel, and with a 32 finish. This cone adapter enables the connection of two modular HPLC column sections with different internal diameters, for instance, a ½ inch unit connected to 1 inch unit, which in turn connects to a 2 inch unit, etc. With the aid of this cone adapter one may use slurry packing preparative columns with particle sizes less than 15 micron. In this case, the wider column is successfully used mainly as a reservoir.

The columned cone adapter as shown in FIG. 19, and in the cross section in FIG. 18, is preferably made of 316 stainless steel and with 32 finish. This cone adapter can be used as a guard column and as a device which disperses the loading sample more uniformly for effecting a better separation. It also may be used on the end of the column to funnel and focus the eluted product. This adapter has basically two uses, intercolumn cone adapter for use in connecting two sections of different internal diameters, and an additional use as an end columned adapter as shown in FIG. 19.

The tap adapter as shown in FIGS. 20 through 27, not only enables the connection of two modular HPLC sections, but has a tap and a special annulus-like frit therebetween so some segment of the eluent can be removed before it enters the next column section. These additional features, the tap and the frit, are capable of selecting the portions and fractions of the mixture allowed to enter the next section without contaminating it with unwanted chemicals.

Another application for the tap adapter is to commence with one type of mobile liquid phase and then use the tap to introduce a different mobile liquid phase, thus effecting pre-purification of the sample in the same overall column.

The frits as shown in FIGS. 5, 6, 9, 10, 11, 17 and 19, are preferably made of 316 stainless steel which is resistant to various solvents and mild buffers, acids and bases (but no HCL) and all organic acids and bases. Obviously other materials may be used, such as ceramic, etc. They lend themselves to easy purification with various solvents. A frit handle may be installed to facilitate handling. These frits are available constructed inherently having various porosities, such as in the range of 1-3 microns, 3-5 microns, 3-10 microns, 7-9 microns, 7-25 microns, and 20-55 microns. In addition, the particles of the column packing material available for use in conjunction with the columns, and for packing therein, and as used in combination with the various frits, may have various particle sizes and pore diameters as follows. For example, packing material is available having a particle size of approximately 5 microns. In addition, packing material having particle size of approximately 10 microns, and a pore diameter of 60 angstroms is available. Furthermore, particle sizes in a range of 15 microns, and pore diameter of 150 angstroms, is also available. In addition, particle sizes in the range of 30 to 70 microns, and having a pore diameter of approximately 275 angstroms, is available. Finally, particle sizes in the range of 40 to 60 microns is likewise available. Regardless of what type of packing material may be utilized, the frits aid in supporting the column support media in their respective column body.

The O-rings are preferably made of Teflon. Actually, the smaller O-ring located on the frit makes the seal, and the larger O-ring is employed for additional safety.

The end plates as shown in FIGS. 28, 29, 30 and 31, are preferably made of 316 stainless steel with a 32 polish. They each have a shallow funnel type shape in the center preferably of about 1°± slope, in order to more evenly spread the liquid charge entering into the column and funneling the eluted liquid from the column. Any male connectors adapter may be used for the corresponding size tubing.

Variations or other modifications and their applications may occur to those skilled in the art upon reviewing the subject mater of this disclosure. Such variations and modifications within the spirit of this invention are intended to be encompassed within the scope of any claims to patent protection issuing upon the same. The description of the preferred embodiment set forth herein, in addition to the drawings as shown, are provided primarily for illustrative purposes only.

Having thus described the invention what is claimed and desired to be secured by Letters Patent is:

1. A chromatography column incorporating at least a pair of column sections and with each column section having terminal flange-like means intergrally connecting at each of its ends, said column sections capable of modularly and axially joining together through their terminal flange-like means, a porous frit, a pair of column sections internally separated by said porous frit, said porous frit incorporating handle means extending approximately centrally and integrally therefrom to facilitate its manipulation, an adapter arranged intermediate a pair of column sections to connect said column sections together, each column section having an internal channel arranged therethrough, and each column section having an inlet and an outlet end, and wherein said adapter arranged connecting intermediate a pair of adjacent column sections, said adapter having a cone-shaped chamber arranged therethrough and being of decreasing diameter along its length, said adapter having O-rings adjacent each side to provide a fluid tight seal with the contiguous flange-like means of the pair of adjacent connecting column sections, said adapter provided for joining modular columns together having differing internal diameters for their formed channels, and end plates for use in conjunction with each column section, each end plate having a central aperture provided therethrough to provide for the entrance or exiting of fluids from the chromatographic column sections during performance of a chromatographic procedure, said end plate having an interior surface connecting against the flange-like means of the adjacent column section, each end plate upon its internal surface having a funnel-like shape communicating with the central aperture formed through the said end plate, a connector attaching with the central aperture formed through the said end plate, and tubing connecting with the connector to facilitate the entrance or removal of fluids from the chromatographic column sections during performance of a chromatographic procedure.

2. The invention of claim 1 and wherein said adapter includes tap means for the removal or injecting of a fluid from within the chromatographic column sections.

* * * * *